United States Patent [19]

Black et al.

[11] Patent Number: 4,774,255

[45] Date of Patent: Sep. 27, 1988

[54] PYROGLUTAMIC ACID ESTERS, THEIR SYNTHESIS AND USE IN TOPICAL PRODUCTS

[75] Inventors: John G. Black, Bedford; Ian R. Scott, Northamptonshire, both of England

[73] Assignee: Lever Brothers Company, New York, N.Y.

[21] Appl. No.: 764,170

[22] Filed: Aug. 9, 1985

[30] Foreign Application Priority Data

Aug. 20, 1984 [GB] United Kingdom ................ 8421112

[51] Int. Cl.⁴ .................... A61K 31/40; C07D 207/12; C07D 403/12; C07D 403/14
[52] U.S. Cl. ................................. 514/423; 514/422; 548/518; 548/519; 548/534
[58] Field of Search ........................ 548/534, 518, 519; 514/422, 423

[56] References Cited

U.S. PATENT DOCUMENTS

| Re. 29,003 | 10/1976 | Furlenmeier et al. | 540/340 |
| 3,839,322 | 10/1974 | Furlenmeier et al. | 540/340 |
| 3,956,323 | 5/1976 | Furlenmeier et al. | 546/170 X |
| 3,957,758 | 5/1976 | Furlenmeier et al. | 540/340 |

FOREIGN PATENT DOCUMENTS

| 48-82046 | 11/1983 | Japan . |
| 591505 | 9/1977 | Switzerland . |
| 1377304 | 12/1974 | United Kingdom . |

OTHER PUBLICATIONS

J. G. Barrett and I. R. Scott, (1983) "Pyrrolidone Carboxylic Acid Synthesis in Guinea Epidermis", J. Invest. Dermatol. 81 122–124.

I. R. Scott-C. R. Harding and J. G. Barrett (1982) "Histidine-rich Protein of the Keratohyaline Granules", Bio. Chem.

Chemical Abstract 98:77945 (JF-A-57 91933-Pola Chemical Industries Inc.).

"Chemistry of Organic Compounds", Carl R. Noller, 3rd Edition, 1965.

Primary Examiner—Donald G. Daus
Assistant Examiner—William A. Teoli, Jr.
Attorney, Agent, or Firm—James J. Farrell; Gerard J. McGowan

[57] ABSTRACT

Esters of pyroglutamic acid having the structure:

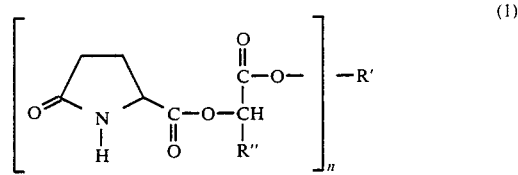

(1)

where R' and R" are the same or different and are each represented by H or the grouping $$CH_3[(CH_2)_w(CHCH_3)_x(CHOH)_y(CH=CH)_z]-$$

where
n is an integer of from 1 to 3
w is zero, or an integer of from 1 to 21
x is zero, or an integer of from 1 to 4
y is zero, or an integer of from 1 to 2
z is zero, or an integer of from 1 to 4
provided that the total number of carbon atoms in each of said grouping will not exceed 22;
and provided also that when the subgrouping (CH=CH) is present, then the total number of carbon atoms in said grouping will be from 16 to 22. Synthesis, and uses of the said esters in topical compositions are also provided.

17 Claims, No Drawings

PYROGLUTAMIC ACID ESTERS, THEIR SYNTHESIS AND USE IN TOPICAL PRODUCTS

The invention relates to esters of pyroglutamic acid, their synthesis and their use in products for topical application to human skin as precursors of pyroglutamic acid.

COMPOUNDS PER SE

Accordingly the invention provides esters of pyroglutamic acid having the structure:

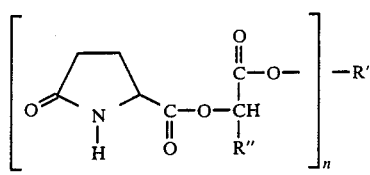 (1)

where R' and R" are the same or different and are each represented by H or the grouping:

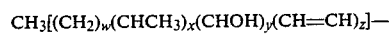

where
 n is an integer of from 1 to 3
 w is zero, or an integer of from 1 to 21
 x is zero, or an integer of from 1 to 4
 y is zero, or an integer of from 1 to 2
 z is zero, or an integer of from 1 to 4
 provided that the total number of carbon atoms in each of said grouping will not exceed 22;
 and provided also that when the subgrouping (CH=CH) is present, then the total number of carbon atoms in the said grouping will be from 16 to 22.

Examples of the grouping:

 are:

methyl
ethyl
propyl
iso-propyl
butyl
iso-butyl
tert-butyl
valeryl
iso-valeryl
caproyl
heptyl caprylyl
capryl
lauryl
myristyl
palmityl
stearyl
arachidyl
behenyl
hydroxy methyl
2-hydroxy ethyl
2-hydroxy propyl
3-hydroxy propyl
2-hydroxy butyl
3-hydroxy butyl
4-hydroxy butyl
5-hydroxy valeryl
6-hydroxy caproyl
2,3-dihydroxy propyl
2,3-dihydroxy butyl
12-hydroxy stearyl
linoleoyl
linolenoyl
arachidonoyl It is to be understood that the above list is not exhaustive, there being many other examples of alkyl or substituted alkyl radicals expressed by the above generic grouping.

Specific examples of esters of pyroglutamic acid are:
2-pyroglutamyl propionic acid
methyl-2-pyroglutamyl acetate
ethyl-2-pyroglutamyl propionate
ethyl-2-pyroglutamyl n-butyrate
ethyl-2-pyroglutamyl n-valerate
ethyl-2-pyroglutamyl n-caproate
ethyl-2-pyroglutamyl n-heptylate
ethyl-2-pyroglutamyl n-caprylate
ethyl-2-pyroglutamyl n-pelargonate
ethyl-2-pyroglutamyl-3-hydroxybutyrate
iso-propyl-2-pyroglutamyl propionate
iso-propyl-2-pyroglutamyl n-caprylate
n-propyl-2-pyroglutamyl propionate
n-propyl-2-pyroglutamyl n-caprylate
glyceryl mono(2-pyroglutamyl n-caprylate)
glyceryl mono(2-pyroglutamyl propionate)
glyceryl di(2-pyroglutamyl propionate)
lauryl-2-pyroglutamyl n-caprylate
stearyl-2-pyroglutamyl n-caprylate
stearyl-2-pyroglutamyl propionate
12-hydroxystearyl-2-pyroglutamyl propionate
stearyl-2-pyroglutamyl stearate
palmityl-2-pyroglutamyl propionate
linoleoyl-2-pyroglutamyl propionate, and
linoleoyl-2-pyroglutamyl n-caprylate.

It is to be understood that the above list of specific examples of esters of pyroglutamic acid is not exhaustive, there being many other examples expressed by the generic structure of these esters.

SYNTHESIS OF COMPOUNDS PER SE

The invention also provides a process for the synthesis of esters of 2-pyroglutamic acid which comprises the steps of:

(i) reacting pyroglutamic acid with an acid ester having the structure:

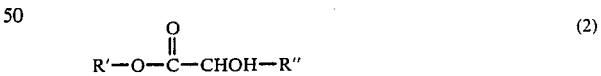 (2)

where R' and R" are the same or different and are each represented by H or the grouping:

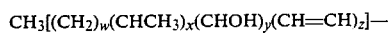

where
 w is zero, or an integer of from 1 to 21
 x is zero, or an integer of from 1 to 4
 y is zero, or an integer of from 1 to 2
 z is zero, or an integer of from 1 to 4
 provided that the total number of carbon atoms in each of said grouping will not exceed 22;
 and provided also that when the subgrouping (CH=CH) is present, then the total number of carbon atoms in the said grouping will be from 16 to 22; and (ii) isolating the ester of pyroglutamic acid so obtained.

It will be appreciated that when R' in the above structure is H, then the product of step (i) in the above process will be an acid having the structure:

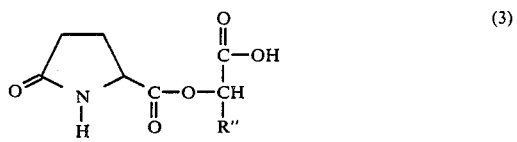

It will then be necessary to condense this acid (3) with an alcohol having the structure:

R'OH where R' is represented by the grouping $CH_3[(CH_2)_w(CHCH_3)_x(CHOH)_y(CH=CH)_z]-$ in order to obtain the ester of pyroglutamic acid according to the invention having the structure (1).

Pyroglutamic acid and the acid or ester having the structure:

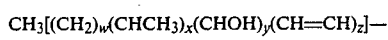

can be reacted in the dry state by heating the mixture, preferably at a pressure of less than that of atmospheric pressure. It may, however, be more convenient to react pyroglutamic acid and the ester in the presence of an organic solvent and/or a drying agent.

This aspect of the invention is illustrated by the following examples.

EXAMPLE 1

Synthesis of ethyl-2-pyroglutamyl propionate

Ethyl 2-pyroglutamyl propionate was prepared on a small scale by refluxing tritiated pyroglutamic acid with a 10 to 20 molar excess of ethyl 2-hydroxy propionate in xylene. Anhydrous magnesium sulphate was added to remove water. After 48 hours, volatile fractions were removed by rotary evaporation and ethyl 2-pyroglutamyl propionate was isolated by thin layer chromatography on silica gel H. The structure of the isolated ester of pyroglutamic acid was confirmed by mass spectrometry and its radio chemical purity by thin layer chromatography.

EXAMPLE 2

Synthesis of ethyl-2-pyroglutamyl n-valerate

The procedure of Example 1 was repeated except that the ester employed was ethyl-2-hydroxy valerate.

EXAMPLE 3

Synthesis of ethyl-2-pyroglutamyl n-caproate

The procedure of Example 1 was repeated except that the ester employed was ethyl-2-hydroxy caproate.

EXAMPLE 4

Synthesis of ethyl-2-pyroglutamyl n-caprylate

The procedure of Example 1 was repeated except that the ester employed was ethyl-2-hydroxy caprylate.

EXAMPLE 5

Synthesis of iso-propyl-2-pyroglutamyl propionate 2 moles of iso-propyl lactate were refluxed with 1 mole of pyroglutamic acid in toluene with a Dean-Stark water entrainer for 72 hours. The reaction mix was cooled, filtered and rotary evaporated to leave an involatile oil containing the ester of pyroglutamic acid.

iso-Propyl-2-pyroglutamyl propionate was isolated by preparative scale high performance liquid chromatography using a hexane:ethanol gradient on a normal phase silica column. Its purity was confirmed by analytical high performance liquid chromatography and its structure by mass spectrometry.

EXAMPLE 6

Synthesis of iso-propyl-2-pyroglutamyl n-butyrate

The procedure described in Example 5 can be repeated using iso-propyl-2-hydroxy n-butyrate as the ester instead of iso-propyl lactate.

EXAMPLE 7

Synthesis of iso-propyl-2-pyroglutamyl n-caprylate

The procedure described in Example 5 was repeated except that the ester employed was iso-propyl-2-hydroxy n-caprylate.

EXAMPLE 8

Synthesis of glyceryl mono-(2-pyroglutamyl n-caprylate)

3 g of pyroglutamic acid was mixed with 3 g of 2-hydroxy caprylic acid and heated at from 140° to 150° C. for three hours under 20 mm pressure. The resulting 2-pyroglutamyl n-caprylic acid was partially purified by extraction with ethyl ether followed by separation with petroleum ether (boiling point 40°-60° C.). The ester concentrated in the lower phase was dried in a stream of nitrogen.

An excess of glycerol was added to the dried 2-pyroglutamyl n-caprylic acid, heated at from 140° to 150° C. for 3 hours at 20 mm pressure. The reaction mixture was cooled, extracted with 50% hexane, 50% ethanol and separated by preparative high peformance liquid chromatography using a normal phase silica column and a gradient of hexane/ethanol. The isolated glyceryl mono-(2-pyroglutamyl n-caprylate) was checked for purity by analytical high performance liquid chromatography and for structure by mass spectrometry.

EXAMPLE 9

Synthesis of lauryl-2-pyroglutamyl n-caprylate

The procedure as described in Example 8 was repeated except that in place of glycerol, lauryl alcohol was used.

EXAMPLE 10

Synthesis of stearyl-2-pyroglutamyl n-caprylate

The procedure as described in Example 8 was repeated except that in place of glycerol, stearyl alcohol was used.

EXAMPLE 11

Alternative synthesis of ethyl-2-pyroglutamyl propionate

A mixture of 500 g pyroglutamic acid, 1,000 ml ethyl 2-hydroxy propionate (ethyl lactate) and 1000 ml toluene were refluxed in a Dean-Stark apparatus for 48 hours. Toluene and excess ethyl lactate were then removed by rotary evaporation and the residue distilled under vacuum (21 0.5 mm Hg). The initial distillate contained residual ethyl lactate and ethyl pyroglutamic acid as a byproduct. The final distillate, a slightly yellow viscous liquid, was pure ethyl-2-pyroglutamyl propionate.

In some of the foregoing examples, tritiated pyroglutamic acid was employed as one of the starting materials to confirm the purity of the isolated pyroglutamyl ester and to enable the fate of the tritiated ester of pyroglutamic acid to be ascertained when it is applied to skin, by locating tritiated pyroglutamic acid resulting from skin enzyme activity.

TOPICAL COMPOSITIONS

The invention further provides a composition for topical application to human skin which comprises an effective amount of from 0.01 to 99% by weight of an ester of pyroglutamic acid as herein defined together with a physiologically and cosmetically acceptable diluent. These compositions preferably comprise from 0.1 to 20%, most preferably from 0.5 to 5% by weight of the ester.

The esters of pyroglutamic acid are those as defined herein. The preferred esters for use in topical compositions according to the invention are:

2-pyroglutamyl propionic acid
methyl-2-pyroglutamyl acetate
ethyl-2-pyroglutamyl propionate
ethyl-2-pyroglutamyl n-butyrate
ethyl-2-pyroglutamyl n-valerate
ethyl-2-pyroglutamyl n-caproate
ethyl-2-pyroglutamyl n-heptylate
ethyl-2-pyroglutamyl n-caprylate
ethyl-2-pyroglutamyl n-pelargonate
ethyl-2-pyroglutamyl-3-hydroxybutyrate
iso-propyl-2-pyroglutamyl propionate
iso-propyl-2-pyroglutamyl n-caprylate
n-propyl-2-pyroglutamyl propionate
n-propyl-2-pyroglutamyl n-caprylate
glyceryl mono(2-pyroglutamyl n-caprylate)
glyceryl mono(2-pyroglutamyl propionate)
glyceryl di(2-pyroglutamyl propionate)
lauryl-2-pyroglutamyl n-caprylate
stearyl-2-pyroglutamyl n-caprylate
stearyl-2-pyroglutamyl propionate
12-hydroxystearyl-2-pyroglutamyl propionate
stearyl-2-pyroglutamyl stearate
palmityl-2-pyroglutamyl propionate
linoleoyl-2-pyroglutamyl propionate, and
linoleoyl-2-pyroglutamyl n-caprylate.

The physiologically and cosmetically acceptable diluent can be water, physiological saline or any suitable organic solvent in which the ester is soluble or dispersible.

The composition can be a simple solution or dispersion or a gel or a cream.

The composition according to the invention can be applied topically to human skin in order to moisturise the skin and to leave it in a soft supple condition. The composition is accordingly particularly beneficial in remoisturising dry skin or for the treatment of chapped or detergent-damaged skin. The composition can also be employed in the topical treatment of acne comedones, pimples and spots, and in the topical treatment of ichthyosis, hyperkeratosis and psoriasis, and also for the topical treatment of sunburn.

In Japanese patent KOKAI No. 48-82046, published November 1973, moisturising and softening compositions are disclosed, these compositions containing as effective constituents pyrrolidone carboxylates represented by the following formula:

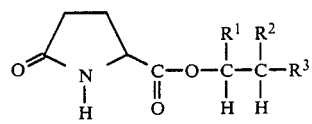

or

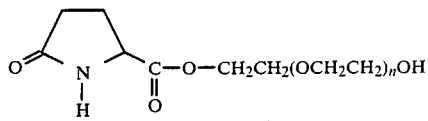

where
$R^1$ is H, $CH_3$ or $CH_2Oh$
$R^2$ is H or OH
$R^3$ is $H_1$, $CH_3$, $CH_2OH$, $CH_2CH_3$, $CH(OH)CH_3$ or $CH_2CH_2OH$
n is the integer 1 or 2; and
the total number of carbon atoms in $R^1$ and $R^3$ is 1 or 2, and
the total of OH groups is 1 or 2.

MODE OF ACTION OF THE ESTERS

Pyroglutamic acid (also known as 2-pyrrolidone-5-carboxylic acid) is the principal ingredient of the "natural moisturising factor" that enables the stratum corneum of the skin to maintain a high water content despite low external humidity. Pyroglutamic acid applied topically to the skin has a temporary moisturising effect but it is easily washed away and gives no long term skin benefit.

The esters of pyroglutamic acid according to the invention are analogues of naturally occurring n-terminal pyroglutamic acid peptides. These naturally occurring peptides are substrates for the enzyme pyroglutamic acid peptidase which represents one route of pyroglutamic acid synthesis in the stratum corneum. (see: J G Barrett & I R Scott 1983 "Pyrrolidone carboxylic acid synthesis in guinea pig epidermis." J Invest. Dermatol. 81, 122). It has been discovered that the esters according to the invention readily penetrate into the stratum corneum, and there provide a substrate for this enzyme at the normal site of pyroglutamic acid synthesis, that is, inside the cells of the stratum corneum.

The amount of pyroglutamic acid produced naturally in the stratum corneum is strictly limited by the amount of a preformed protein precursor accumulated by the stratum corneum cell while it is undergoing development (see: I R Scott, C R Harding & J G Barrett (1982) "Histidine-rich protein of the keratohyalin granules: source of free amino acids, urocanic acid and pyrrolidone carboxylic acid in the stratum corneum". Biochim. Biophys-Acta 719, 110). Treatment of the skin with the esters according to the invention can therefore allow the skin to produce, using its own synthetic machinery, higher levels of pyroglutamic acid than would otherwise be possible.

Because pyroglutamic acid is thereby produced within the cells of the stratum corneum, it is very resistant to removal by washing, a significant fraction remaining after a continuous 2 hour period of water washing.

Enzyme action on the esters according to the invention liberates not only pyroglutamic acid but also free alpha-hydroxy acids which also have proven skin benefit properties.

QUANTITATIVE DATA ON EFFICACY

In an in vitro laboratory test, ethyl-2-pyroglutamyl propionate labelled with $^3$H on the pyroglutamic acid residue was applied as a 1% solution in ethanol to newborn rat skin held in a glass cell, allowing the dermal side of the skin to be bathed in a buffered salts solution while the epidermal surface was exposed to normal atmospheric conditions. At intervals of 24 hours, samples of skin were taken and washed with continuous agitation in several changes of water at room temperature.

Interfollicular epidermis was removed from these skin pieces by "freeze scraping"—which avoids contamination of the sample by follicular tissue or material trapped within the hair follicle. The epidermis was then extracted in methanol and the soluble extract analysed by thin layer chromatography. The amount of tritiated pyroglutamic acid present was calculated as nmoles/cm$^2$ of skin surface.

The results showed that tritiated pyroglutamic acid was produced from the applied tritiated ethyl-2-pyroglutamyl propionate at a rate of 16 nmoles/cm$^2$/day for a period of at least 3 days following the single application. Of the ethyl-2-pyroglutamyl propionate applied, one quarter was converted into pyroglutamic acid over a 24 hour period, and one third of this pyroglutamic acid resisted the continuous period of 2 hours water washing.

The substantivity of tritiated pyroglutamic acid produced by the skin from tritiated ethyl-2-pyroglutamyl propionate was compared with that of tritiated pyroglutamic acid applied directly to the skin and left for the same period of time (24 hours). The percentage of the tritiated pyroglutamic acid remaining in the skin was measured over a sequence of five 20 minute water washes. The results are shown in Table 1 below:

TABLE 1

| | % pyroglutamic acid remaining in epidermis | |
|---|---|---|
| No. of washes | from ethyl-2-pryoglutamyl propionate applied topically | from pyroglutamic acid applied topically |
| 0 | 100 | 100 |
| 1 | 80 | 20 |
| 2 | 40 | 4 |
| 3 | 36 | 3 |
| 4 | 33 | 2 |
| 5 | 31 | 1 |

From these results, it can be seen that a substantial amount of pyroglutamic acid remains in the epidermis after repeated washing when that pyroglutamic acid is derived from ethyl-2-pyroglutamyl propionate according to the invention. When free pyroglutamic acid is applied to the epidermis, it is entirely washed from the tissue after a similar number of repeated washings.

The procedure described above was repeated with other tritiated esters of pyroglutamic acid according to the invention; these are listed in Table 2 below. In each case, these esters were applied to 1 cm$^2$ of newborn rat skin as 10 μl of a 2% solution in ethanol. After 24 hours, the amount of tritiated pyroglutamic acid present in the epidermis in a form resistant to a period of 2 hours continuous washing with water was measured. The quantity of tritiated pyroglutamic acid delivered and retained by the skin in this way is recorded in Table 2 below:

TABLE 2

| Esters of tritiated pyroglutamic acid applied topically | Tritiated pyroglutamic acid delivered to epidermis: nmoles/cm$^2$/day |
|---|---|
| ethyl-2-pyroglutamyl propionate | 25 ± 5 |
| ethyl-2-pyroglutamyl n-valerate | 10.5 ± 4 |
| ethyl-2-pyroglutamyl n-caproate | 12 ± 4 |
| ethyl-2pyroglutamyl n-caprylate | 5 ± 0.5 |

IN VITRO TESTS ON HUMAN SKIN

Initial experiments carried out on human scalp using a similar methodology to that shown above indicate that the rate of production of substantive tritiated pyroglutamic acid is comparable to that obtained using newborn rat skin, being 11 nmoles/cm$^2$/day. The level of naturally occurring pyroglutamic acid in the same samples was measured as 34 nmoles/cm$^2$. A period of three days continuous treatment with the ethyl-2-pyroglutamyl propionate can therefore double the naturally occurring level of pyroglutamic acid in the stratum corneum. Since the normal turnover time of human stratum corneum is 2–3 weeks, the stratum corneum is generating pyroglutamic acid five times faster from ethyl-2-pyroglutamyl propionate than it does from its own endogenous pyroglutamic acid precursors. The pyroglutamic acid delivered from the ester should therefore have significant beneficial effects on the moisture binding properties of the skin.

IN VIVO TESTS ON HUMAN SKIN

An in vivo study using human subjects was carried out according to the following procedure.

A solution of 5% by weight ethyl-2-pyroglutamyl propionate in 10% ethanol:90% water was applied to the upper arm over the biceps each evening for four days. A control solution of 10% ethanol:90% water was applied to the other arm. The arms were washed each evening before application. After this period of application, the arms were allowed to rest for three days with thorough washing of the arms each day.

Sellotape strips were used to sample the superficial stratum corneum on the test sites each day for a further 11 days. The arms were not washed during this period. The pyroglutamic acid content of the tapes strips was measured and expressed as n moles per mg of total protein on the strip, measured by the ninhydrin reaction after acid hydrolysis.

The results given in Table 3 below showed an increase of about 50% in the pyroglutamic acid content of the stratum corneum which persists for up to 11 days from the end of treatment. As this represents approximately the normal turnover time of the stratum corneum, the results show that treatment with ethyl-2-pyroglutamyl propionate increases the pyroglutamic acid content throughout the whole stratum corneum and not merely in the superficial layers.

TABLE 3

| Days since end of treatment | Pyroglutamic acid level in tape strip (nmoles/mg protein) | | Test: Control Ratio |
|---|---|---|---|
| | Test Site | Control Site | |
| 3 | 145 | 86 | 1.69 |
| 4 | 252 | 165 | 1.53 |
| 5 | 410 | 269 | 1.52 |
| 7 | 322 | 256 | 1.26 |
| 8 | 483 | 312 | 1.55 |
| 10 | 435 | 337 | 1.29 |
| 11 | 370 | 322 | 1.15 |
| 13 | 190 | 233 | 0.82 |

A further in vivo study using human subjects was carried out according to the following procedure.

8 volunteers applied a 5% by weight solution of ethyl-2-pyroglutamyl propionate in 10% ethanol:90% water to the back of the hand and upper arm on one side of the body and a control solution of 10% ethanol:90% water to the hand and arm on the other side. Allocation of test and control sides was random, the panellists were not informed which was the test solution.

The applications were made each evening and hands and arms were washed as normal the following day. Treatment continued for 7 days then all treated sites were thoroughly washed.

4 successive tape strips were taken from each treatment site and analysed for pyroglutamic acid and protein. Pyroglutamic acid was expressed as nmoles/mg total protein as in the previously described in vivo study.

Analysis of variance of the results showed that test and control sites differed significantly in pyroglutamic acid level ($P<0.001$). In the case of the hand, treatment with ethyl-2-pyroglutamyl propionate increased pyroglutamic acid level 1.75 times although there was variation in this mean value between the different strips taken from any one site. On the arm, the increase was 2.34 times and was fairly consistent from the first to the last strip.

Compositions containing esters of the invention are further illustrated by the following Examples of topical compositions suitable for application to human skin.

EXAMPLE 12

This example illustrates a high internal phase water-in-oil emulsion containing an ester of the invention.

A high internal phase water-in-oil emulsion having the following formulation was prepared:

| | % w/w |
|---|---|
| Fully hydrogenated coconut oil | 3.9 |
| 2-pyroglutamyl propionic acid | 5 |
| Brij 92* | 5 |
| Bentone 38 | 0.5 |
| Preservative | 0.3 |
| MgSO$_4$ 7H$_2$O | 0.3 |
| Butylated hydroxy toluene | 0.01 |
| Perfume | qs |

-continued

| | % w/w |
|---|---|
| Water to | 100 |

*Brij 92 is polyoxyethylene (2) oleyl ether

EXAMPLE 13

This example illustrates an oil-in-water cream containing an ester of the invention.

An oil-in-water cream emulsion having the following formulation was prepared:

| | % w/w |
|---|---|
| Mineral oil | 4 |
| Ethyl-2-pyroglutamyl propionate | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water to | 100 |

*Brij 56 is cetyl alcohol POE (10)
Alfol 16RD is cetyl alcohol

EXAMPLE 14

This example illustrates an alcoholic lotion containing an ester of the invention.

The lotion had the following formulation:

| | % w/w |
|---|---|
| iso-Propyl-2-pyroglutamyl propionate | 0.2 |
| Ethanol | 40 |
| Perfume | qs |
| Butylated hydroxy toluene | 0.01 |
| Water to | 100 |

EXAMPLE 15

This example illustrates an alcoholic lotion containing an ester of the invention.

The lotion had the following formulation:

| | % w/w |
|---|---|
| Ethyl-2-pyroglutamyl n-caprylate | 1 |
| Dimethylsulphoxide | 10 |
| Ethanol | 40 |
| Antioxidant | 0.1 |
| Perfume | qs |
| Water to | 100 |

EXAMPLES 16 AND 17

The following compositions according to the invention represent lotions which can be used in the treatment of dry skin:

| | % w/w | |
|---|---|---|
| | 16 | 17 |
| Glyceryl mono(2-pyroglutamyl propionate) | 1.5 | — |
| Stearyl-2-pyroglutamyl stearate | — | 0.5 |
| Perfume | 0.1 | 0.1 |
| Hydroxyethyl cellulose | 0.4 | 0.4 |

-continued

|  | % w/w | |
|---|---|---|
|  | 16 | 17 |
| Absolute ethanol | 25 | 25 |
| p-methyl benzoate | 0.2 | 0.2 |
| Sterilised demineralised water to | 100 | 100 |

EXAMPLES 18 AND 19

The following compositions according to the invention represent lotions which can be used in the treatment of dry skin:

|  | % w/w | |
|---|---|---|
|  | 18 | 19 |
| 12-hydroxy-stearyl-2-pyroglutamyl stearate | 8 | — |
| Ethyl-2-pyroglutamyl-3-hydroxy n-butyrate | — | 15 |
| Ethanol | 10 | 10 |
| Perfume | 0.5 | 0.5 |
| Distilled water to | 100 | 100 |

EXAMPLES 20 AND 21

The following compositions according to the invention represent creams which can be used to treat skin burns:

|  | % w/w | |
|---|---|---|
|  | 20 | 21 |
| Methyl-2-pyroglutamyl acetate | 3 | — |
| n-propyl-2-pyroglutamyl n-caprylate | — | 2 |
| Cetyl alcohol | 8 | 8 |
| Mineral oil | 4 | — |
| Paraffin wax | — | 2 |
| Xanthan gum | 0.3 | 0.3 |
| Preservative | 0.4 | 0.4 |
| Perfume | qs | qs |
| Demineralised water to | 100 | 100 |

EXAMPLE 22

This example illustrates a high internal phase water-in-oil emulsion containing an ester of the invention.

A high internal phase water-in-oil emulsion having the following formulation was prepared:

|  | % w/w |
|---|---|
| Fully hydrogenated coconut oil | 3.9 |
| Ethyl-2-pyroglutamyl n-butyrate | 0.5 |
| Brij 92* | 5 |
| Bentone 38 | 0.5 |
| Preservative | 0.3 |
| MgSO$_4$ 7H$_2$O | 0.3 |
| Butylated hydroxy toluene | 0.01 |
| Perfume | qs |
| Water to | 100 |

*Brij 92 is polyoxyethylene (2) oleyl ether

EXAMPLE 23

This example illustrates an oil-in-water cream containing an ester of the invention.

An oil-in-water cream emulsion having the following formulation was prepared:

|  | % w/w |
|---|---|
| Mineral oil | 4 |
| Ethyl-2-pyroglutamyl n-valerate | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 24

This example illustrates an alcoholic lotion containing an ester of the invention.

The lotion had the following formulation:

|  | % w/w |
|---|---|
| iso-Propyl-2-pyroglutamyl n-caprylate | 2 |
| Ethanol | 40 |
| Perfume | qs |
| Butylated hydroxy toluene | 0.01 |
| Water | to 100 |

EXAMPLE 25

This example illustrates an alcoholic lotion containing an ester of the invention.

The lotion had the following formulation:

|  | % w/w |
|---|---|
| Ethyl-2-pyroglutamyl n-caprolate | 0.2 |
| Dimethylsulphoxide | 10 |
| Ethanol | 40 |
| Antioxidant | 0.1 |
| Perfume | qs |
| Water | to 100 |

EXAMPLES 26 AND 27

The following compositions according to the invention represent lotions which can be used in the treatment of dry skin:

|  | % w/w | |
|---|---|---|
|  | 26 | 27 |
| Glyceryl di(2-pyroglutamyl propionate) | 1.5 | — |
| Stearyl-2-pyroglutamyl n-caprylate | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | 100 |

EXAMPLES 28 AND 29

The following compositions according to the invention represent lotions which can be used in the treatment of dry skin:

|  | % w/w | |
|---|---|---|
|  | 28 | 29 |
| Stearyl-2-pyroglutamyl propionate | 0.08 | — |
| n-propyl-2-pyroglutamyl propionate | — | 0.15 |
| Ethanol | 10 | 10 |
| Perfume | 0.5 | 0.5 |
| Distilled water | to 100 | 100 |

EXAMPLES 30 AND 31

The following compositions according to the invention represent creams which can be used to treat skin burns:

|  | % w/w | |
|---|---|---|
|  | 30 | 31 |
| Ethyl-2-pyroglutamyl acetate | 3 | — |
| iso-Propyl-2-pyroglutamyl n-caprylate | — | 2 |
| Cetyl alcohol | 8 | 8 |
| Mineral oil | 4 | — |
| Paraffin wax | — | 2 |
| Xanthan gum | 0.3 | 0.3 |
| Preservative | 0.4 | 0.4 |
| Perfume | qs | qs |
| Demineralised water | to 100 | 100 |

EXAMPLE 32

This example illustrates a high internal phase water-in-oil emulsion containing an ester of the invention.

A high internal phase water-in-oil emulsion having the following formulation was prepared:

|  | % w/w |
|---|---|
| Fully hydrogenated coconut oil | 3.9 |
| ethyl-2-pyroglutamyl iso-butyrate | 1 |
| Brij 92* | 5 |
| Bentone 38 | 0.5 |
| Preservative | 0.3 |
| $MgSO_4\ 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 33

This example illustrates an oil-in-water cream containing an ester of the invention.

An oil-in-water cream emulsion having the following formulation was prepared:

|  | % w/w |
|---|---|
| Mineral oil | 4 |
| Ethyl-2-pyroglutamyl n-pelargonate | 5 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 34

This example illustrates an alcoholic lotion containing an ester of the invention.

The lotion had the following formulation:

|  | % w/w |
|---|---|
| glyceryl mono(2-pyroglutamyl n-caprylate) | 12 |
| Ethanol | 40 |
| Perfume | qs |
| Butylated hydroxy toluene | 0.01 |
| Water | to 100 |

EXAMPLE 35

This example illustrates an alcoholic lotion containing an ester of the invention.

The lotion had the following formulation:

|  | % w/w |
|---|---|
| Palmityl-2-pyroglutamyl propionate | 5 |
| Dimethylsulphoxide | 10 |
| Ethanol | 40 |
| Antioxidant | 0.1 |
| Perfume | qs |
| Water | to 100 |

EXAMPLES 36 AND 37

The following compositions according to the invention represent lotions which can be used in the treatment of dry skin:

|  | % w/w | |
|---|---|---|
|  | 36 | 37 |
| Linoleoyl-2-pyroglutamyl propionate | 15 | — |
| Stearyl-2-pyroglutamyl stearate | — | 10 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | 100 |

EXAMPLES 38 AND 39

The following compositions according to the invention represent lotions which can be used in the treatment of dry skin:

|  | % w/w | |
|---|---|---|
|  | 38 | 39 |
| Linoleoyl-2-pyroglutamyl n-caprylate | 2 | — |
| Lauryl-2-pyroglutamyl n-caprylate | — | 3 |
| Ethanol | 10 | 10 |
| Perfume | 0.5 | 0.5 |

EXAMPLES 40 AND 41

The following compositions according to the invention represent creams which can be used to treat skin burns:

|  | % w/w | |
| --- | --- | --- |
|  | 40 | 41 |
| Methyl-2-pyroglutamyl n-heptylate | 3 | — |
| ethyl-2-pyroglutamyl n-caprylate | — | 2 |
| Cetyl alcohol | 8 | 8 |
| Mineral oil | 4 | — |
| Paraffin wax | — | 2 |
| Xanthan gum | 0.3 | 0.3 |
| Preservative | 0.4 | 0.4 |
| Perfume | qs | qs |
| Demineralised water | to 100 | 100 |

-continued

|  | % w/w | |
| --- | --- | --- |
|  | 38 | 39 |
| Distilled water | to 100 | 100 |

We claim:
1. Ester of pyroglutamic acid chosen from:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate.

2. The ester of claim 1 wherein the ester is ethyl-2-pyroglutamoyloxy propionate.

3. The ester of claim 1 wherein the ester is ethyl 2-pyroglutamoyloxy n-butyrate.

4. The ester of claim 1 wherein the ester is ethyl-2-pyroglutamyl n-valerate.

5. The ester of claim 1 wherein the ester is iso-propyl-2-pyroglutamoyloxy propionate.

6. The ester of claim 1 wherein the ester is n-propyl-2-pyroglutamoyloxy propionate.

7. An ester of pyroglutamic acid selected from:
glyceryl mono(2-pyroglutamoyloxy propionate),
glyceryl di(2-pyroglutamoyloxy propionate), or
glyceryl mono(2-pyroglutamoyloxy n-caprylate).

8. A composition for topical treatment of human skin which comprises an effective amount of from 0.01 to 79% by weight of an ester of pyroglutamic acid having the structure:

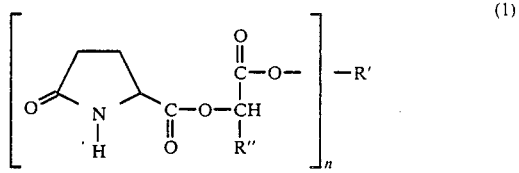

where R' and R" are the same or different and are each represented by H or the grouping:

$$CH_3[(CH_2)_w(CHCH_3)_x(CHOH)_y(CH=CH)_z]-$$

where
n is an integer of from 1 to 3;
w is zero, or an integer of from 1 to 21;
x is zero, or an integer of from 1 to 4;
y is zero, or an integer of from 1 to 2;
z is zero, or an integer of from 1 to 4
provided that the total number of carbon atoms in each of said grouping will not exceed 22;
and provided also that when the subgrouping (CH=CH) is present, then the total number of carbon atoms in said grouping will be from 16 to 22, together with a physiologically and cosmetically acceptable diluent.

9. The composition of claim 8, which further comprises a sunscreen agent.

10. The composition of claim 8, which is a solution, dispersion, gel or cream.

11. The composition of claim 8, wherein the grouping:

$$CH_3[(CH_2)_w(CHCH_3)_x(CHOH)_y(CH=CH)_z]-$$

is chosen from
methyl
ethyl
n-propyl
iso-propyl
n-butyl
iso-butyl
n-valeryl
iso-valeryl
caproyl
n-heptyl
caprylyl
capryl
lauryl
myristyl
palmityl
stearyl
arachidyl
behenyl
2-hydroxy ethyl
2-hydroxy-n-propyl
3-hydroxy-n-propyl
2-hydroxy-n-butyl
3-hydroxy butyl
4-hydroxy butyl
2,3-dihydroxy-n-propyl
2,3-dihydroxy-n-butyl
12-hydroxystearyl
linoleyl
linolenyl, and arachidonyl.

12. The composition of claim 8 wherein the ester is:
glyceryl mono(2-pyroglutamoyloxy propionate)
glyceryl di(2-pyroglutamoyloxy propionate), or
glyceryl mono(2-pyroglutamoyloxy n-caprylate).

13. The composition of claim 8 wherein the ester is ethyl-2-pyroglutamoyloxy propionate.

14. The composition of claim 8 wherein the ester is ethyl 2-pyroglutamoyloxy n-butyrate.

15. The composition of claim 8 wherein the ester is ethyl-2-pyroglutamoyloxy n-valerate.

16. The composition of claim 8 wherein the ester is iso-propyl-2-pyroglutamoyloxy propionate.

17. The composition of claim 8 wherein the ester is n-propyl-2-pyroglutamoyloxy propionate.

* * * * *

UNITED STATES PATENT AND TRADEMARK OFFICE
CERTIFICATE OF CORRECTION

PATENT NO. : 4,774,255
DATED : September 27, 1988
INVENTOR(S) : Black et al.

It is certified that error appears in the above—identified patent and that said Letters Patent is hereby corrected as shown below:

Claim 8, line 3 replace "79" with --99--

Signed and Sealed this

Twenty-fourth Day of October, 1989

Attest:

DONALD J. QUIGG

Attesting Officer

Commissioner of Patents and Trademarks